(12) United States Patent
Kim et al.

(10) Patent No.: US 7,614,313 B2
(45) Date of Patent: Nov. 10, 2009

(54) METHOD OF GENERATING AND MEASURING TORSIONAL WAVES IN CYLINDRICAL STRUCTURE USING MAGNETOSTRICTIVE EFFECT, AND MAGNETOSTRICTIVE TRANSDUCER AND STRUCTURE DIAGNOSIS APPARATUS USING THE METHOD

(75) Inventors: Yoon-Young Kim, Seoul (KR); Seung-Hyun Cho, Ansan-si (KR); Ik-Kyu Kim, Seoul (KR); Chan-Il Park, Gunpo-si (KR)

(73) Assignee: Seoul National University Industry Foundation, Seoul (KR)

( * ) Notice: Subject to any disclaimer, the term of this patent is extended or adjusted under 35 U.S.C. 154(b) by 597 days.

(21) Appl. No.: 11/524,326

(22) Filed: Sep. 21, 2006

(65) Prior Publication Data
US 2007/0090904 A1    Apr. 26, 2007

(30) Foreign Application Priority Data
Oct. 20, 2006   (KR) .................... 10-2005-0099220

(51) Int. Cl.
*G01L 3/02*   (2006.01)

(52) U.S. Cl. .............................. 73/862.333; 73/862.331
(58) Field of Classification Search .................
73/862.331–862.336
See application file for complete search history.

(56) References Cited

U.S. PATENT DOCUMENTS

| | | | |
|---|---|---|---|
| 5,022,275 A * | 6/1991 | Satoh et al. ............ | 73/862.335 |
| 6,624,628 B1 * | 9/2003 | Kwun et al. ................ | 324/240 |
| 7,215,118 B2 * | 5/2007 | Park et al. .................. | 324/238 |
| 7,295,001 B2 * | 11/2007 | Kim et al. .................. | 324/209 |

* cited by examiner

*Primary Examiner*—Max Noori
(74) *Attorney, Agent, or Firm*—The Nath Law Group; Jerald L. Meyer; Derek Richmond

(57) ABSTRACT

A method and apparatus for generating and measuring a torsional wave in a rod, shaft or pipe using magnetostriction are provided. The magnetostrictive transducer includes at least one strip attached to a predetermined position of a rod member, an insulator disposed around the strip, a coil wound around the insulator, and magnets providing a bias magnetic field to the strip, wherein a plurality of strips are attached to the rod member at predetermined intervals in a circumferential direction, and one pole of the magnet is close to an end of a first strip among the plurality of strips, and another pole of the magnet is close to an end of a second strip among the plurality of strips.

11 Claims, 12 Drawing Sheets

METHOD OF GENERATING AND MEASURING TORSIONAL WAVES IN CYLINDRICAL STRUCTURE USING MAGNETOSTRICTIVE EFFECT, AND MAGNETOSTRICTIVE TRANSDUCER AND STRUCTURE DIAGNOSIS APPARATUS USING THE METHOD

This application claims priority from Korean Patent Application No. 10-2005-99220 filed on Oct. 20, 2005 in the Korean Intellectual Property Office, the disclosure of which is incorporated herein by reference in its entirety.

BACKGROUND OF THE INVENTION

1. Field of the Invention

The present invention relates to a magnetostrictive transducer for generating torsional waves in a rod member using magnetostriction, and receiving a signal transmitted by the rod member due to an inverse magnetostrictive effect.

2. Description of the Related Art

Magnetostriction or the Joule effect is an effect in which a physical change occurs in ferromagnetic materials when they are subjected to a magnetic field. The reciprocal effect, the change of the internal magnetic state of ferromagnetic materials when they are subjected to a mechanical stress, is called the Villari effect.

A transducer using magnetostrictive effect can measure changes in an object without making physical contact with the object, and is thus used in diverse fields where contact sensors cannot be used. Ultrasonic waves that can be generated in a waveguide, such as a rod or a pipe, include longitudinal waves, lateral waves, and torsional waves.

Figure 1:
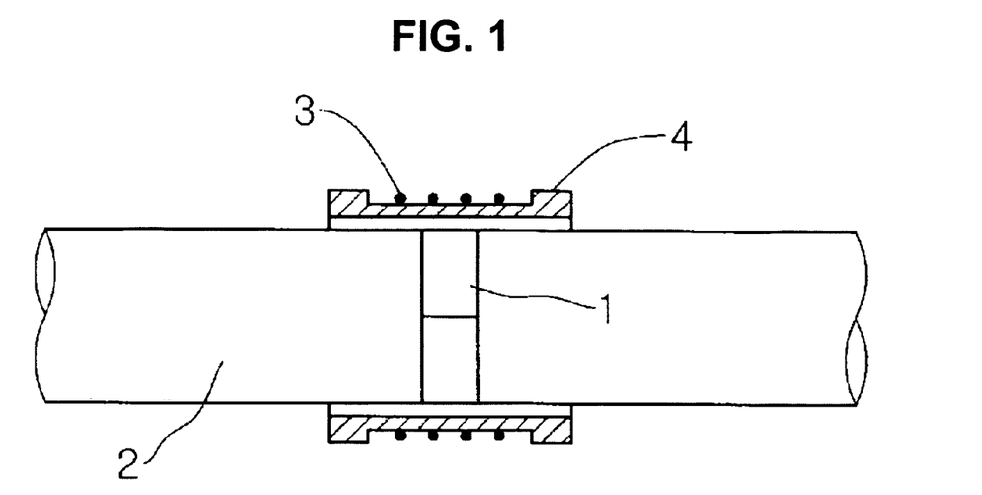
FIG. 1 illustrates a conventional magnetostrictive transducer.

Referring to FIG. 1, a conventional magnetostrictive torsional wave transducer includes a thin strip 1 wound around a rod member 2 in a direction perpendicular to the axis of the rod member 2, an insulator 4 wrapped around the strip 1, and a coil 3 wound around the insulator 4. The strip 1 is made of a ferromagnetic material such as nickel, iron, cobalt, or an alloy of them.

When torsional waves are generated using the conventional magnetostrictive transducer to diagnose a defect in the rod member 2, the strip 1 is fixed around a cylindrical pipe and then the strip 1 is rubbed in the circumferential direction using a permanent magnet or the like to magnetize the ferromagnetic strip 1. A magnetic field is applied around the magnetized strip 1 via the coil 3, thereby generating an elastic wave. When the magnetic field is applied to the strip 1, a torsional wave is induced in the rod member 2. The torsional wave propagates through the rod member 2, and is reflected at an end or a structural defect of the rod member 2. The magnetic field around the strip 1 changes due to the reflected torsional wave, and this change can be measured.

As described above, in the conventional magnetostrictive transducer, a bias magnetic field is generated when the strip 1 is rubbed with a permanent magnet in a circumferential direction. However, when pre-magnetization is achieved by rubbing the strip 1, the degree of magnetization is not the same at every point of the strip, and it is difficult to form a uniform magnetic field throughout the strip 1. In addition, when a large amount of current is applied, the intensity and direction of the initial magnetic field changes, and therefore, re-magnetization is required. In particular, a rod member, such as an oil pipeline, is buried underground, it is not easy to approach, and it is difficult to repeatedly re-magnetize the strip 1. Most of all, the quantity of the magnetization of the strip can be increased by the direct supply of external magnetic field.

Accordingly, a method that efficently magnetizes the strip 1 without having to rub is required. In other words, it is highly desirable to develop a method of generating/measuring a torsional wave more effectively by providing a bias magnetic field in the strip 1 in a stable, continuous manner.

SUMMARY OF THE INVENTION

The present invention provides a method and an apparatus of efficiently generating/measuring a torsional wave in a rod member.

The present invention also provides a method and an apparatus of stably and continuously providing a bias magnetic field to a magnetostrictive transducer.

According to an aspect of the present invention, there is provided a magnetostrictive transducer including at least one strip attached at a predetermined position of a rod member, an insulator disposed around the strip, a coil wound around the insulator, and at least one magnet providing a bias magnetic field to the strip, wherein a plurality of strips are attached to the rod member at a predetermine interval in a circumferential direction, one pole of the magnet is close to an end of a first strip among the plurality of strips, and another pole of the magnet is close to an end of a second strip among the plurality of strips.

According to another aspect of the present invention, there is provided a magnetostrictive transducer for generating and measuring a torsional wave, the magnetostrictive transducer including at least one strip attached at a predetermined position of a rod member, an insulator disposed around the strip, a coil wound around the insulator, and a magnet providing a bias magnetic field to the strip, wherein a plurality of strips are attached to the rod member at a predetermine interval in a circumferential direction, at least two magnets are attached for each strip, one pole of a first magnet among the at least two magnets is attached to an outside of an end portion of the strip, and a different pole of a second magnet among the at least two magnets is attached to an outside of another end of the strip.

These and other objects of the present invention will be described in or be apparent from the following description of the preferred embodiments.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

The present invention will now be described more fully with reference to the accompanying drawings, in which preferred embodiments of the invention are shown. Advantages and features of the present invention and methods of accomplishing the same may be understood more readily by reference to the following detailed description of preferred embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Like reference numerals refer to like elements throughout the specification.

The present invention suggests a method of providing a stable bias magnetic field by appropriately arranging permanent magnets in a new magnetostrictive transducer that generates and measures a torsional wave in a rod, shaft or pipe member using a ferromagnetic strip.

Figure 2:
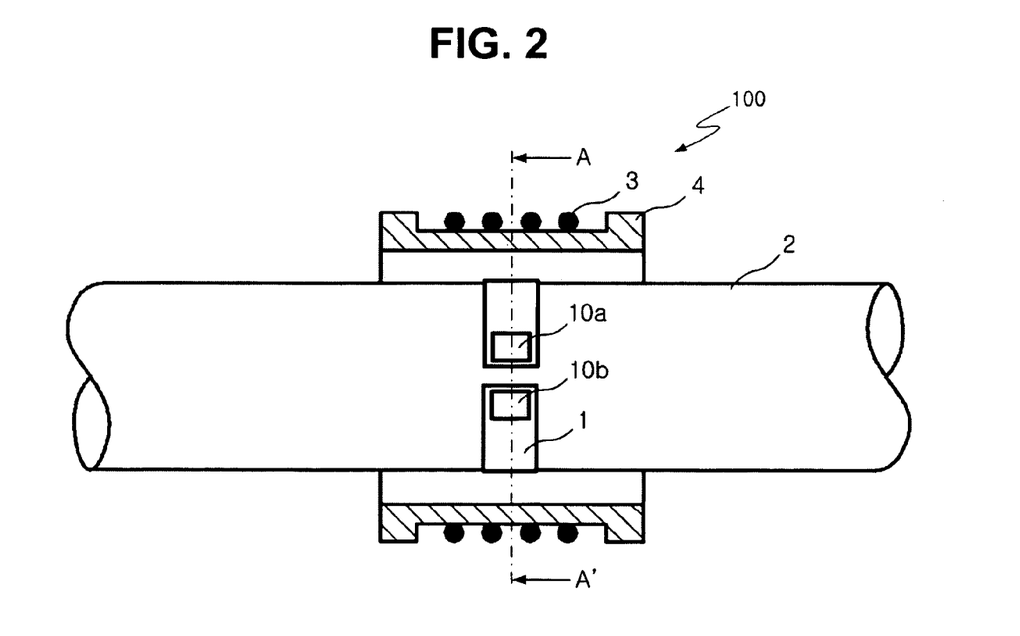
FIG. 2 illustrates a transducer according to an embodiment of the present invention.

FIG. 2 illustrates a transducer 100 according to an embodiment of the present invention. The transducer 100 may include a ferromagnetic strip 1 attached to a rod member 2, an insulator 4 wound a predetermined distance around the strip 1, a driving coil 3 wound around the outer circumference of the insulator 4 to generate a driving magnetic field according to an applied current, and permanent magnets 10a and 10b attached to predetermined positions of the strip 1 to provide a bias magnetic field in a circumferential direction of the strip 1. The strip 1 may be made of a ferromagnetic material such as iron, nickel, cobalt, or an alloy of them, which undergoes significant magnetostriction.

The term "rod member" denotes any object having a much longer length than width, such as a rod, a beam, a shaft, or a hollow pipe.

When variable current flows in the driving coil 3, a magnetic flux is generated through the inside of the insulator 4 due to magnetic induction. The magnetic flux passes through the strip 1. Then, a torsional wave is generated in the rod member 2 due to the magnetostriction of the strip 1.

In order to generate a stable torsional wave in the transducer 100, a bias magnetic field needs to be provided. Accordingly, hereafter, the arrangement of permanent magnets will be described in various embodiments of the present invention.

Figure 3:
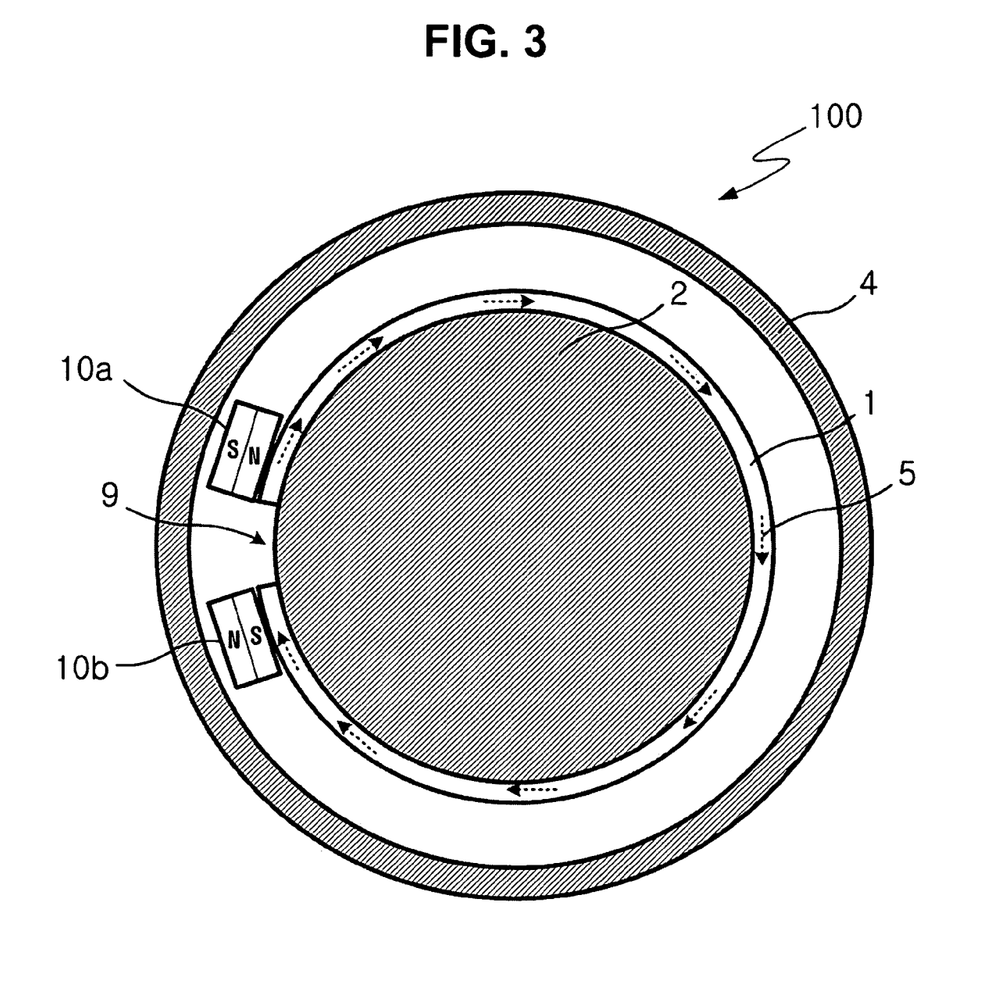
FIG. 3 is a cross-sectional view of the transducer, taken along the line A-A' shown in FIG. 2.

FIG. 3 is a cross-sectional view of the transducer 100 taken along the line A-A' shown in FIG. 2.

The strip 1 is attached a predetermined distance around the outer circumference of the rod member 2, and has a clearance 9 in order to form a path for a magnetic flux. One pole of each of the respective permanent magnets 10a and 10b is attached to either end portion of the strip 1. A path from the N-pole of the permanent magnet 10a to the S-pole of the permanent magnet 10b is formed through the ferromagnetic strip 1. Accordingly, a magnetic flux 5 flows along this path. In other words, a bias magnetic field is formed in the strip 1.

If the cross-section of the rod member 2 has a small area, a satisfactory bias magnetic field can be generated with only a pair of the permanent magnets 10a and 10b, as shown in FIG. 3. However, if the cross-section of the rod member 2 has a large area, the structure shown in FIG. 3 needs to be changed.

Figure 4:
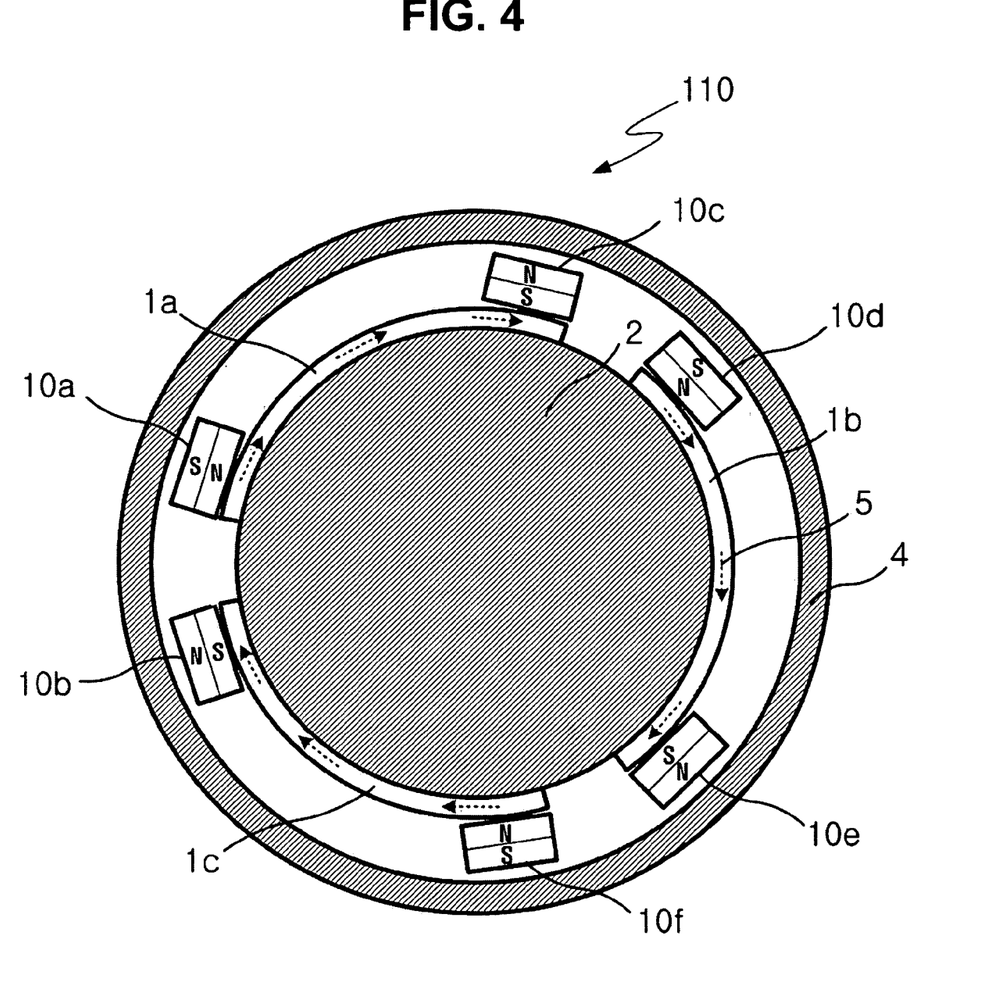
FIG. 4 illustrates a transducer according to another embodiment of the present invention.

FIG. 4 illustrates a transducer 110 including a plurality of strips 1a, 1b, and 1c and a plurality of pairs of permanent magnets 10a, 10b, 10c, 10d, 10e, and 10f, according to an embodiment of the present invention. Referring to FIG. 4, a pair of permanent magnets are disposed at both end portions, respectively, of each strip to form a magnetic flux within the strip. As shown in FIG. 4, when a plurality of strips and a plurality of pairs of permanent magnets are disposed at equal intervals in a circumferential direction of the rod member 2, a satisfactory bias magnetic field can be provided even for a rod member 2 having a large cross-sectional area.

The number of strips and the number of permanent magnets may vary with the cross-sectional area of the rod member 2 and the desired strength of the bias magnetic field to the strips.

In the embodiment shown in FIG. 4, only one pole of each permanent magnet is used. For example, a magnetic flux coming from the N-pole of the permanent magnet 10d goes into the S-pole of the permanent magnet 10e and forms a magnetic field within the strip 1b. However, since the magnetic field of the S-pole of the permanent magnet 10d or the N-pole of the permanent magnet 10e travels through air having a low permeability, some leakage occurs.

Figure 5:
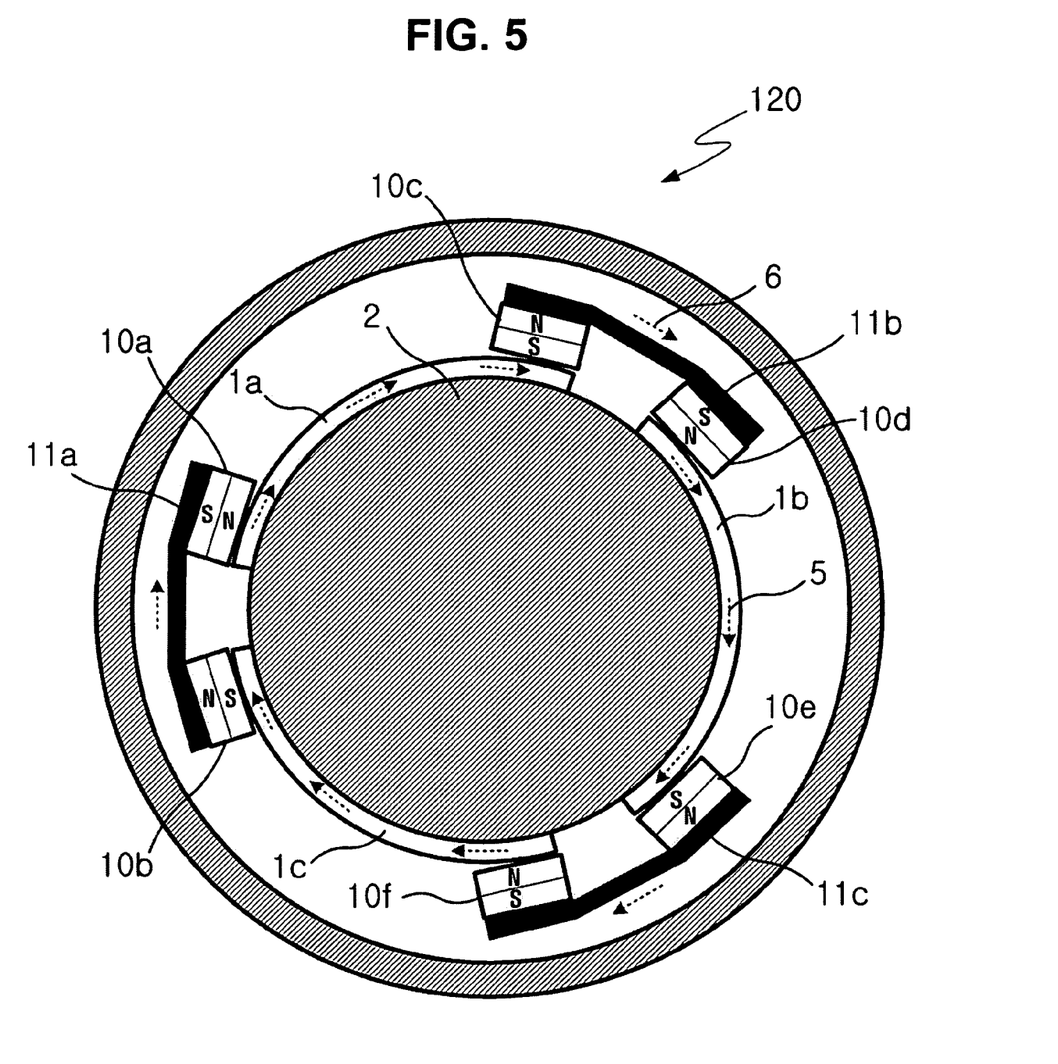
FIG. 5 illustrates a transducer according to still another embodiment of the present invention.

Considering this fact, a method for decreasing the leakage and concentrating the magnetic field by means of a transducer 120 is provided, as shown in FIG. 5.

In the transducer 120 shown in FIG. 5, yokes 11a, 11b, and 11c are used to connect poles of the permanent magnets 10a, 10b, 10c, 10d, 10e, and 10f, which are not used in the transducer 110 shown in FIG. 4, thereby increasing the intensity of a magnetic field generated in the strips 1a, 1b, and 1c. The yokes 11a, 11b, and 11c may be made using a material having a large magnetic permeability to allow the magnetic field to be efficiently guided. This fact is also applied to yokes that are described in the following.

Poles at outer sides (i.e., poles facing a direction opposite to the center of the rod member 2) of adjacent permanent magnets respectively attached to different strips are connected by the yokes 11a, 11b, or 11c. Accordingly, a magnetic flux 6 generated by the poles at the outer sides of the permanent magnets 10a, 10b, 10c, 10d, 10e, and 10f can also be indirectly provided to the strips 1a, 1b, and 1c in addition to the magnetic flux 5 generated by the inner poles attached to the strips 1a, 1b, and 1c.

Figure 6:
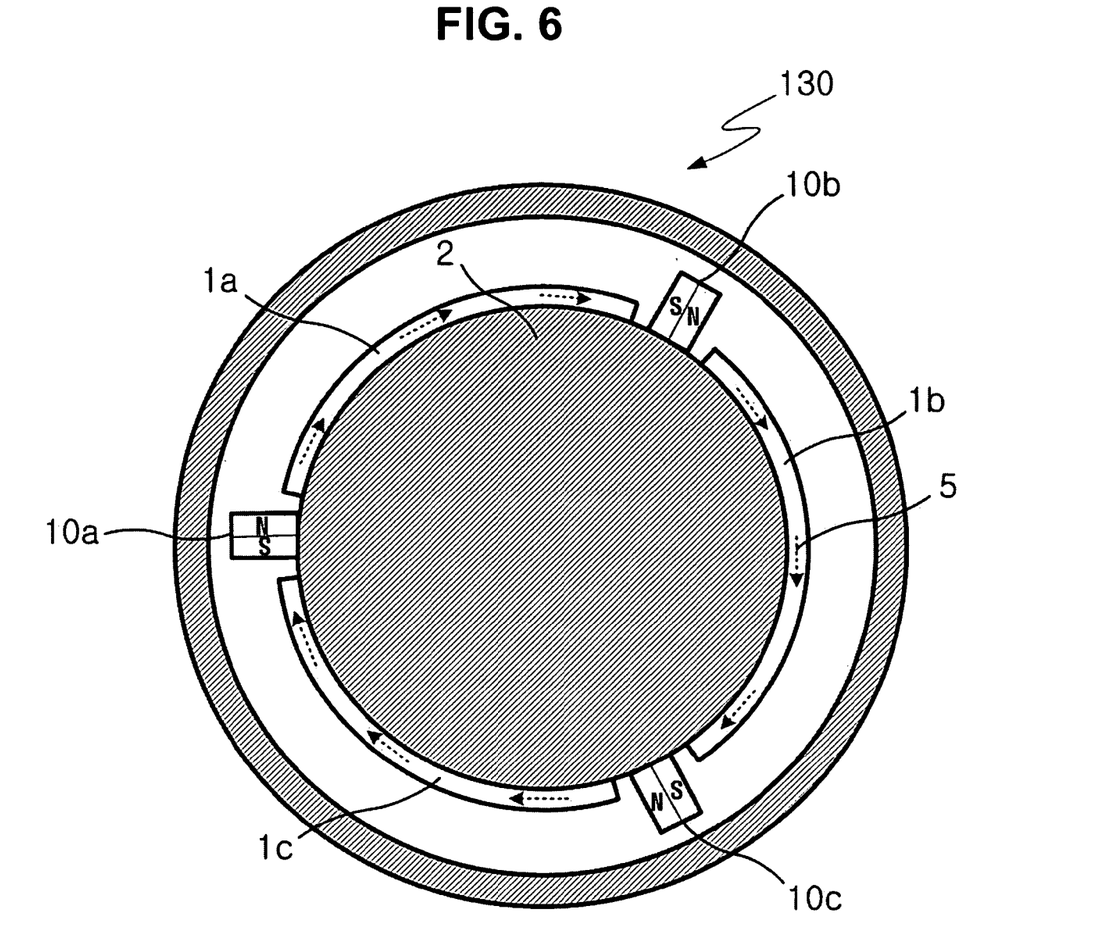
FIG. 6 illustrates a transducer according to yet another embodiment of the present invention.

FIG. 6 illustrates a transducer 130 according to an embodiment of the present invention. One pole of each permanent magnet 10a, 10b, or 10c is close to an end of the strip 1a, 1b, or 1c and the other pole thereof is close to an end of an adjacent one among the strips 1a, 1b, and 1c. The poles are close enough to the strips 1a, 1b, and 1c enough that a magnetic flux between the permanent magnets 10a, 10b, and 10c and the ends of the strips 1a, 1b, and 1c is continuous. The permanent magnets 10a, 10b, and 10c may contact the ends of the strips 1a, 1b, and 1c.

While two permanent magnets are used for each strip 1a, 1b, or 1c in the embodiments shown in FIGS. 3 through 5, only one permanent magnet is used for each of the strips 1a, 1b, and 1c in the embodiment shown in FIG. 6. In addition, all poles of the permanent magnets 10a, 10b, and 10c are close to the strips 1a, 1b, and 1c. As a result, the transducer 130 experiences less loss of magnetic flux than the transducers 100, 110, and 120.

For example, a magnetic flux flowing along the strip 1b goes into the S-pole of the permanent magnet 10c, comes out from the N-pole of the permanent magnet 10c, and then goes into the strip 1c. As a result, the strips 1a, 1b, and 1c and the permanent magnets 10a, 10b, and 10c are combined into one loop, which induces the spontaneous flow of magnetic flux and, therefore, the efficiency of the transducer 130 is increased.

Figure 7:
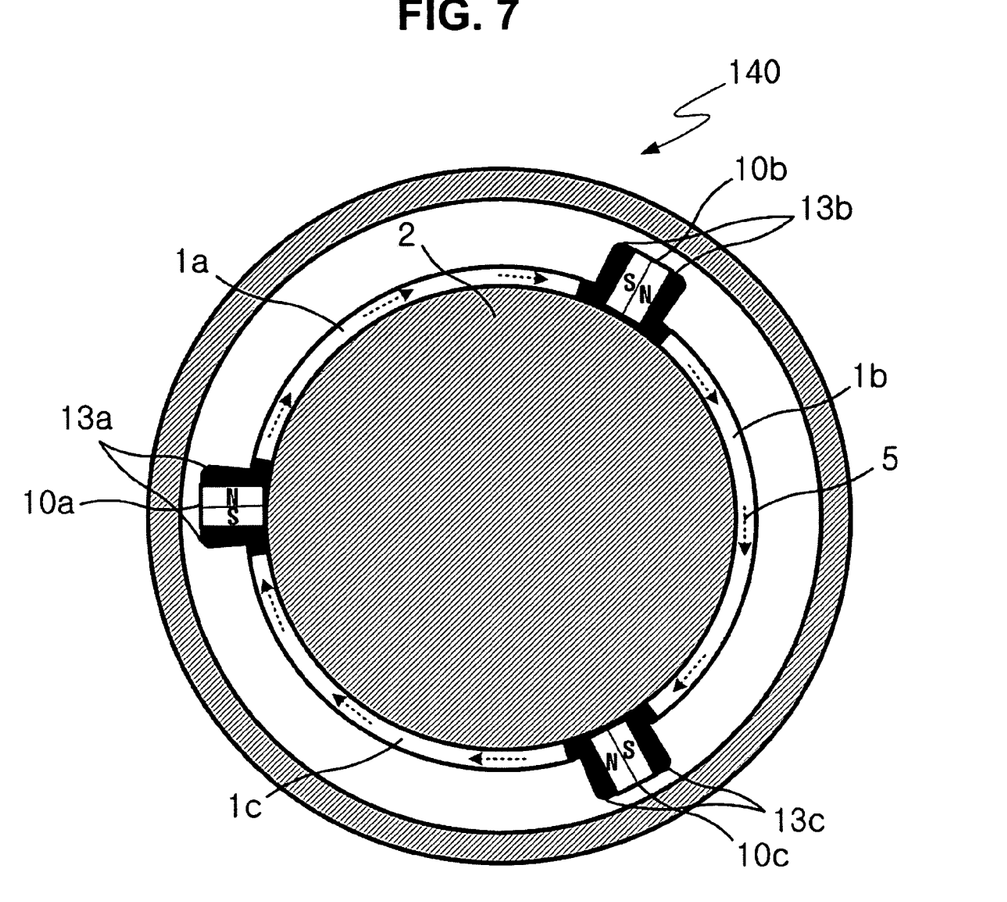
FIG. 7 illustrates a transducer according to a further embodiment of the present invention.

FIG. 7 illustrates a transducer 140, which is a modification of the transducer 130 shown in FIG. 6. The transducer 140 shown in FIG. 7 is fundamentally similar to the transducer 130 shown in FIG. 6, with the exception that the permanent magnets 10a, 10b, and 10c do not directly contact the strips 1a, 1b, and 1c but are maintained a close distance from the strips 1a, 1b, and 1c via yokes 13a, 13b, and 13c. The yokes 13a, 13b, and 13c are used to decrease the leakage of the magnetic flux at the permanent magnets 10a, 10b, and 10c.

Figure 8:
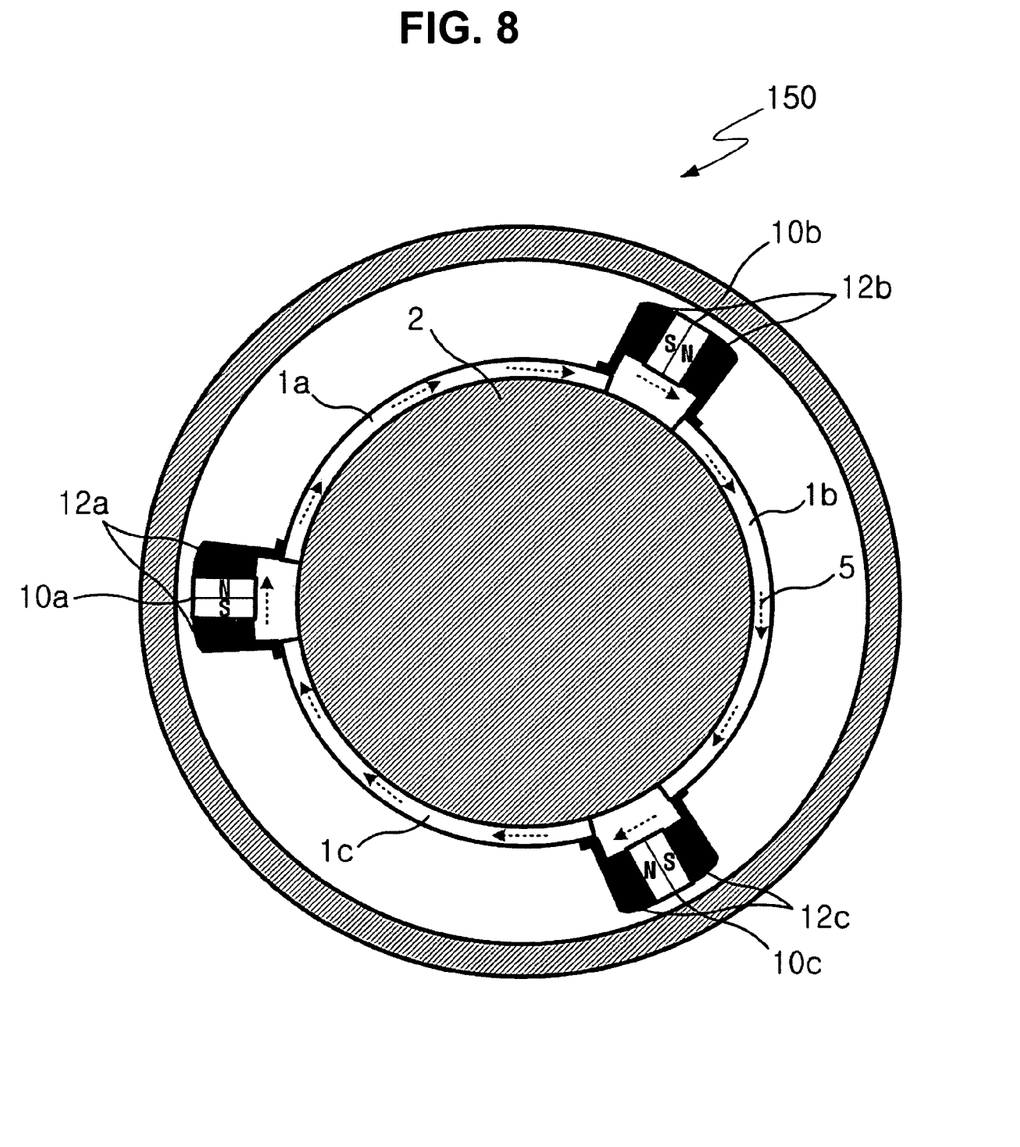
FIG. 8 illustrates a transducer according to another embodiment of the present invention.

FIG. 8 illustrates a transducer 150 according to an embodiment of the present invention. Referring to FIG. 8, adjacent strips are connected via one of the permanent magnets 10a, 10b, and 10c and one yoke pair 12a, 12b, or 12c, but the permanent magnets 10a, 10b, and 10c do not directly contact the rod member 2. The transducer 150 is designed for the case where it is preferable that the magnets do not directly contact the rod member 2.

In the above-described embodiments, the permanent magnets 10a, 10b, and 10c are installed at the side of the rod member 2.

Figure 9:
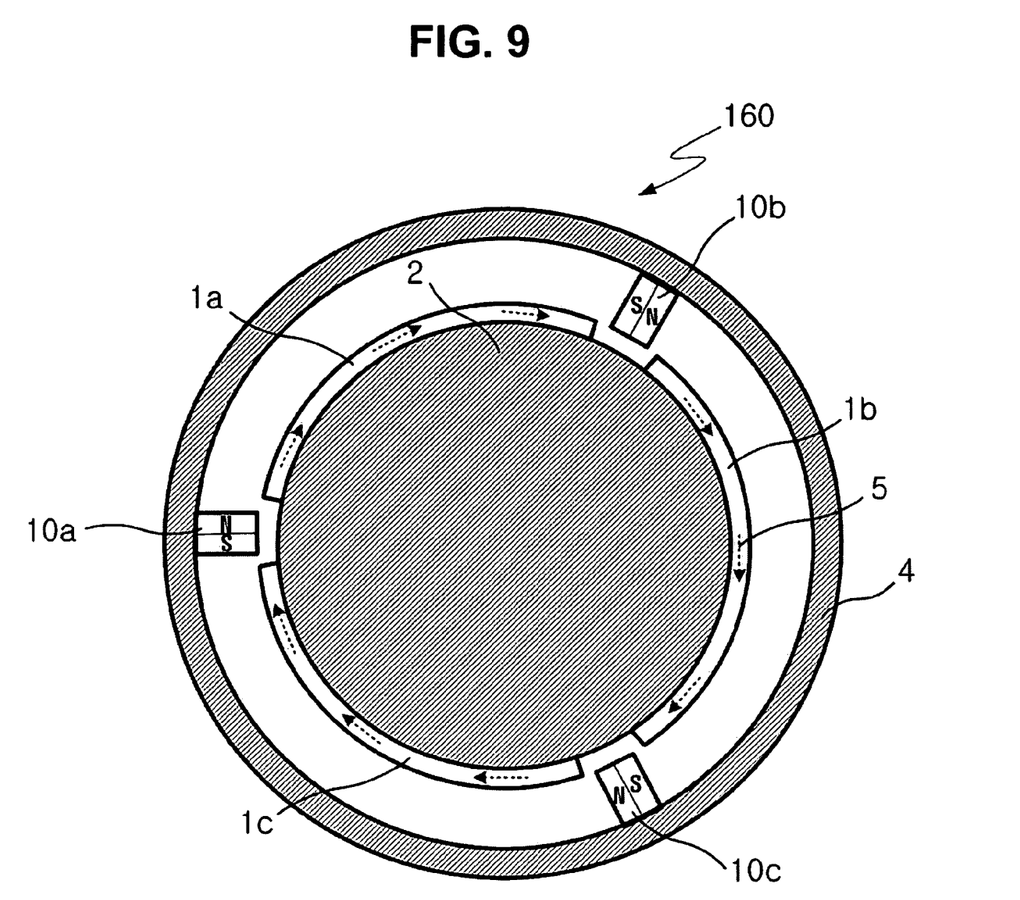
FIG. 9 illustrates a transducer according to still another embodiment of the present invention.

However, the permanent magnets 10a, 10b, and 10c may be installed on the inside of the insulator 4, which is wound a predetermined distance around the rod member 2, as shown in FIG. 9, because contact between the permanent magnets 10a, 10b, and 10c and the strips 1a, 1b, and 1c is not indispensable for inducing a magnetic flux in the strips 1a, 1b, and 1c.

When only the strips 1a, 1b, and 1c are attached to the rod member 2 and the permanent magnets 10a, 10b, and 10c are attached to the inside of the insulator 4, as shown in FIG. 9, the difficulty of manufacturing the transducer 160 so that the permanent magnets 10a, 10b, and 10c properly contact the rod member 2 is eliminated.

However, when the permanent magnets 10a, 10b, and 10c are attached to the inside of the insulator 4, the distance between the permanent magnets 10a, 10b, and 10c and the rod member 2 may be too large.

Figure 10:
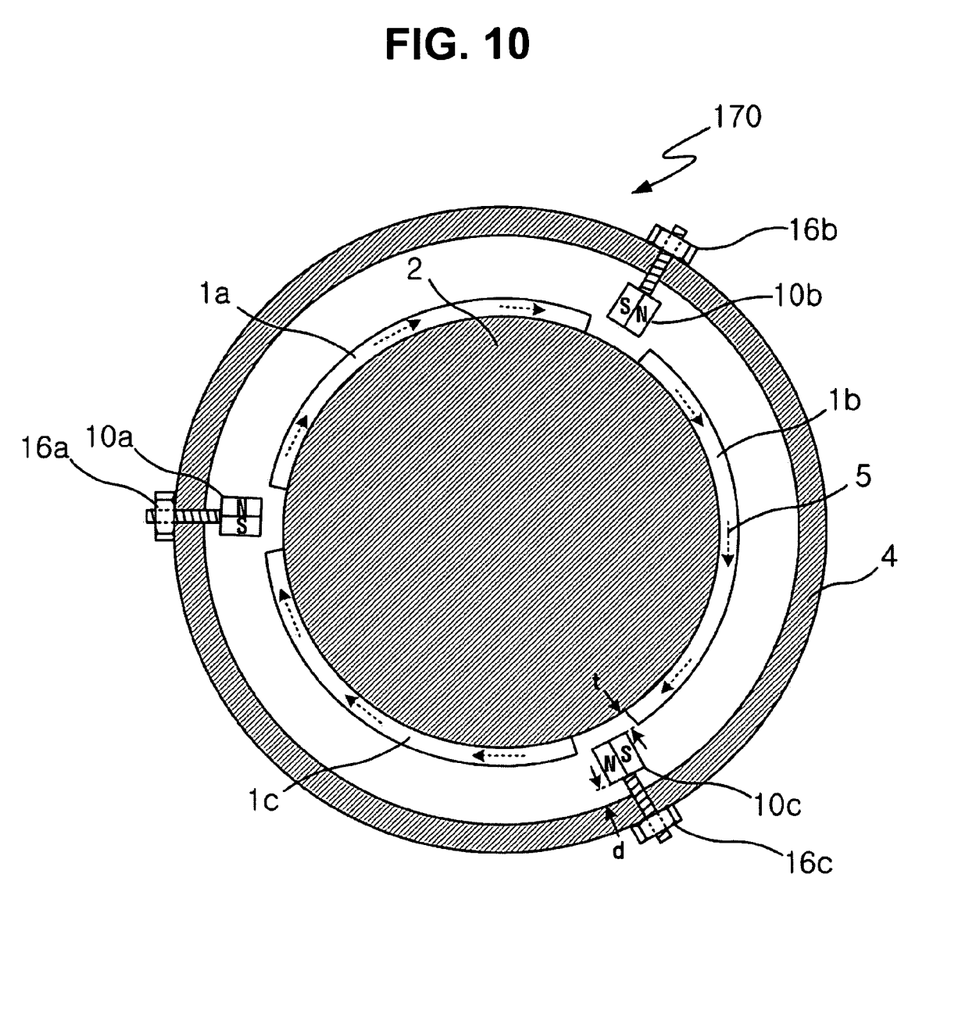
FIG. 10 illustrates a transducer according to yet another embodiment of the present invention.

As such, position adjustors 16a, 16b, and 16c may be further provided at the insulator 4, as shown in FIG. 10. In the transducer 170 shown in FIG. 10, a user can easily adjust the distance between the permanent magnets 10a, 10b, and 10c and the rod member 2 and the distance between the permanent magnets 10a, 10b, and 10c and the insulator 4 when necessary. The position adjustors 16a, 16b, and 16c are simply implemented as a screw and nut assembly, but they can be implemented in various ways.

Figure 11:
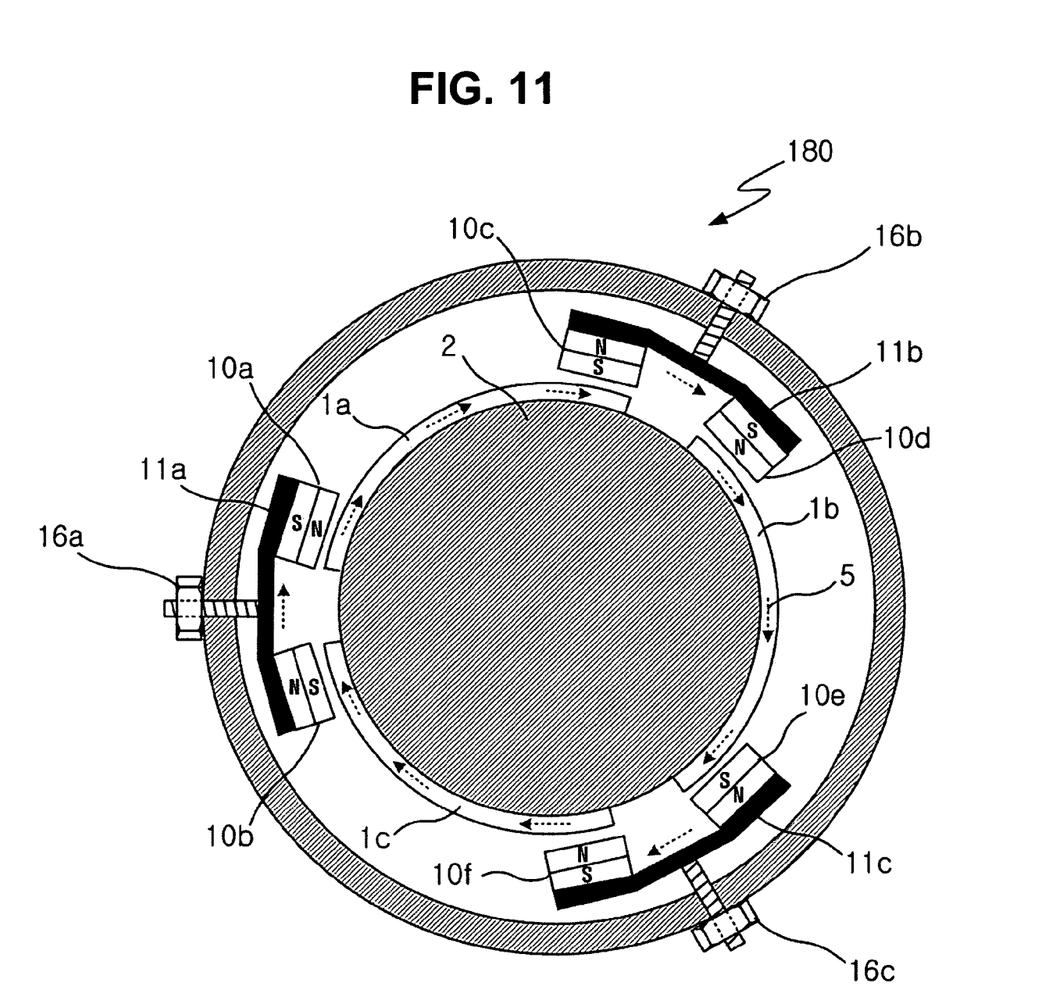
FIG. 11 illustrates a transducer according to a further embodiment of the present invention.

Similarly, when the position adjustors 16a, 16b, and 16c are further provided to the transducer 120 shown in FIG. 5, thereby forming a transducer 180 shown in FIG. 11, positions of the yokes 11a, 11b, and 11c and the permanent magnets 10a, 10b, and 10c attached thereto can be adjusted. In the above-described embodiments, permanent magnets are used as magnets for providing a bias.

However, the present invention is not restricted thereto, and electromagnets may be used instead of the permanent magnets. In this case, all or some of the permanent magnets shown in FIGS. 3 through 11 may be replaced with a corresponding number of electromagnets.

Figure 12:
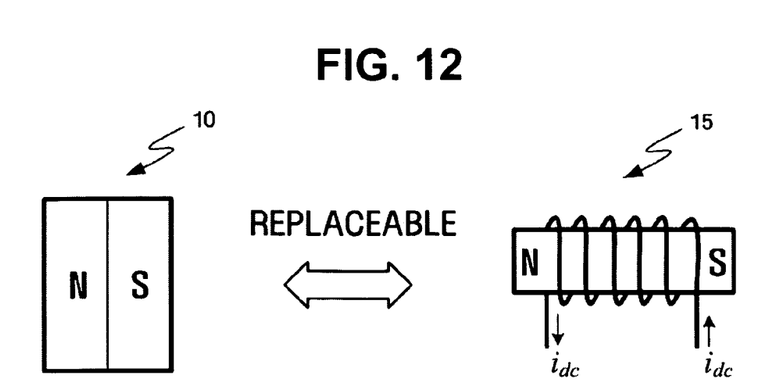
FIG. 12 illustrates an electromagnet that can replace a permanent magnet in an embodiment of the present invention.

FIG. 12 illustrates an electromagnet 15 that can replace a permanent magnet 10 in an embodiment of the present invention. The electromagnet 15, which generates a magnetic field having a predetermined intensity when direct current (DC) is applied to a solenoid, is physically equivalent to the permanent magnet 10. The electromagnet 15 and the permanent magnet 10 can replace each other when necessary, but the electromagnet 15 increases the price of a transducer because the electromagnet 15 makes the structure of the transducer complicated and it requires a DC power supply.

Figure 13:
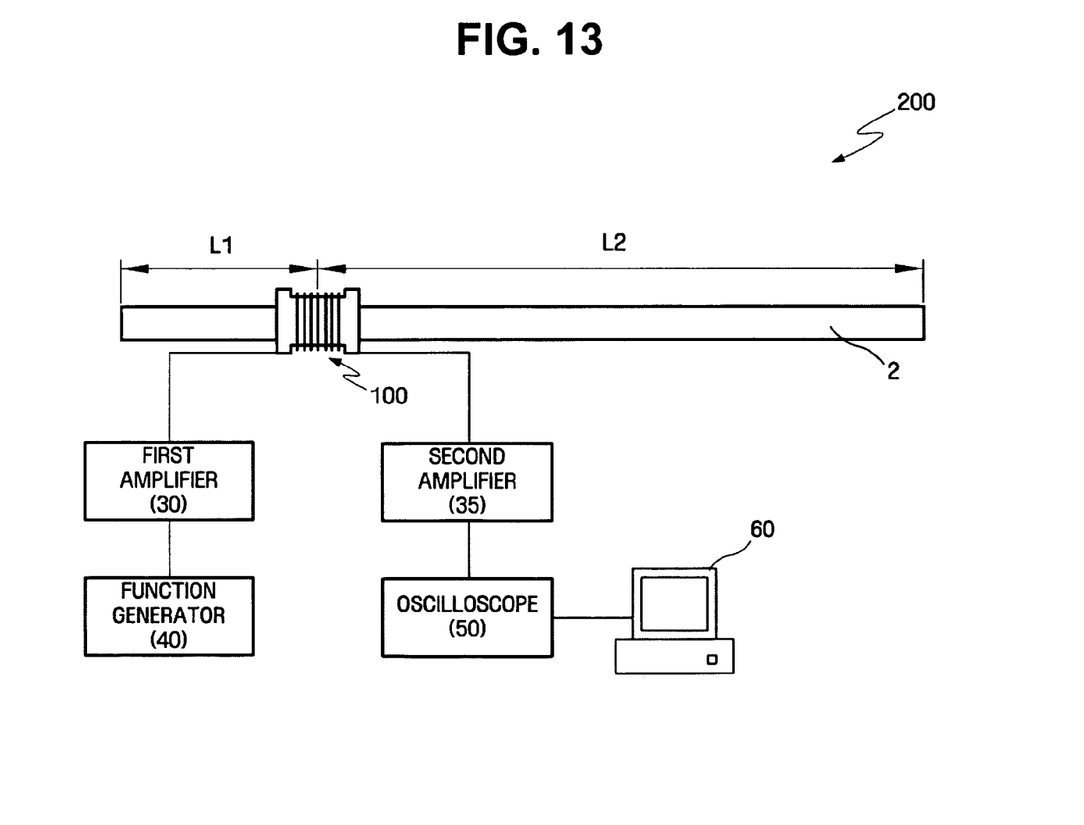
FIG. 13 illustrates a structure diagnosis apparatus according to an embodiment of the present invention.

FIG. 13 illustrates a structure diagnosis apparatus 200 made by connecting various devices to the transducer 100 according to an embodiment of the present invention.

A function generator 40 generates a waveform desired by a user. The waveform is input to an first amplifier 30.

The first amplifier 30 is connected to the transducer 100. The first amplifier 30 amplifies a driving current having the waveform generated by the function generator 40, and applies the amplified driving current to the transducer 100. Here, a bias magnetic field, which acts in a circumferential direction of the rod member 2 due to a magnet according to an embodiment of the present invention, and a variable magnetic field acting in an axial direction of the rod member 2 are simultaneously applied to a strip. As a result, the strip generates a torsional wave in the rod member 2 through magnetostriction.

Meanwhile, a second amplifier 35 receives and amplifies a voltage signal induced by the torsional wave reflected from ends or cracks of the rod member 2.

The waveform of the amplified current and the amplified voltage signal may be input to an oscilloscope 50. The oscilloscope 50 allows a user to check the waveform.

A computer 60 controls the first amplifier 30, the second amplifier 35, the function generator 40, and the oscilloscope 50 according to the user's command and receives and analyzes a signal waveform stored in the oscilloscope 50.

Figure 14:
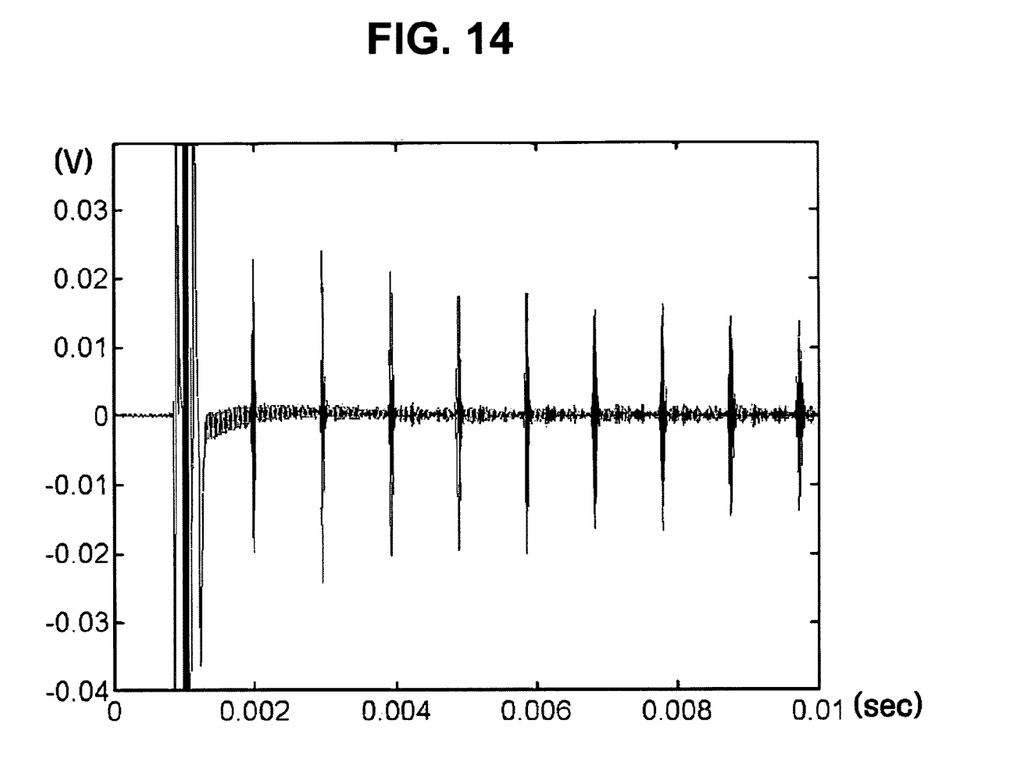
FIG. 14 is a graph showing a voltage generated by a torsional wave reflected from a rod member over time.

FIG. 14 is a voltage-time graph showing a voltage generated by a torsional wave reflected from the rod member 2, which was measured in an experiment using the structure diagnosis apparatus 200 shown in FIG. 13.

In the experiment, the rod member 2 was a pipe having an outer diameter of 50 mm, a length of 3 m, and a thickness of 1.3 mm. A transducer was positioned at the center of the pipe, that is, L1 and L2 shown in FIG. 13 were both 1.5 m.

Referring to FIG. 14, a reflected torsional wave is detected at intervals of about 0.001 seconds, and has a satisfactorily large strength of about 0.02 V, although the strength decreases a little over time. Here, it can be inferred that the generated torsional wave can be transmitted over 100 m if the reflected torsional wave is measured for a longer time.

When the rod member 2 is a long pipe having a length of several kilometers, a transducer according to an embodiment of the present invention may be installed around the rod member 2 at predetermined intervals. When a long pipe has the same cross-sectional area as that the rod member 2 used in the experiment, and the transducer is installed at intervals of about 50 m, it is estimated that the waveform shown in FIG. 14 will be the result. However, when a plurality of transducers are installed at a single rod member, a signal transmitted from other transducers should be filtered.

According to the present invention, a stable torsional wave can be generated and measured continuously at low cost, and the accuracy of the transducer diagnosis can be increased.

While the present invention has been particularly shown and described with reference to exemplary embodiments thereof, it will be understood by those of ordinary skill in the art that various changes in form and details may be made therein without departing from the spirit and scope of the present invention as defined by the following claims. Therefore, it is to be understood that the above-described embodiments have been provided only in a descriptive sense and will not be construed as placing any limitation on the scope of the invention.

What is claimed is:

1. A magnetostrictive transducer for generating and measuring a torsional wave, the transducer comprising:
    at least one strip attached at a predetermined position of a rod member;
    an insulator disposed around the strip;
    a coil wound around the insulator; and
    at least one magnet providing a bias magnetic field to the strip,
    wherein a plurality of strips are attached to the rod member at predetermined intervals in a circumferential direction, and one pole of the magnet is close to an end of a first strip among the plurality of strips, and another pole of the magnet is close to an end of a second strip among the plurality of strips.

2. The magnetostrictive transducer of claim 1, wherein the magnet is attached to the rod member.

3. The magnetostrictive transducer of claim 1, wherein the magnet is attached to an inner wall of the insulator.

4. The magnetostrictive transducer, of claim 1, further comprising a yoke between the magnet and the strip.

5. The magnetostrictive transducer of claim 1, wherein the magnet is one of a permanent magnet and an electromagnet.

6. The magnetostrictive transducer of claim 1, wherein the rod member is one among a beam, a shaft, a hollow pipe, and a pivot.

7. The magnetostrictive transducer of claim 1, wherein the strip is made of one material among nickel, iron, cobalt, and alloys of them, which can exhibit magnetostriction.

8. The magnetostrictive transducer of claim 1, wherein the magnet is attached to the rod member or an inner wall of the insulator.

9. The magnetostrictive transducer of claim 1, further comprising a position adjustor installed in the insulator to adjust a distance between the magnet and the rod member.

10. A magnetostrictive transducer for generating and measuring a torsional wave, the transducer comprising:
    at least one strip attached at a predetermined position of a rod member;
    an insulator disposed around the strip;
    a coil wound around the insulator; and
    at least two magnets providing a bias magnetic field to the strip,
    wherein a plurality of strips are attached to the rod member at a predetermined interval in a circumferential direction, at least two magnets are attached to each strip, one pole of a first magnet among the at least two magnets is attached to an outside of an end portion of the strip, and a different pole of a second magnet among the at least two magnets is attached to an outside of another end of the strip.

11. The magnetostrictive transducer of claim 10, further comprising a ferromagnetic yoke connecting adjacent magnets attached to different strips.

* * * * *